United States Patent [19]

Juguin et al.

[11] Patent Number: 5,160,497
[45] Date of Patent: Nov. 3, 1992

[54] PHENOL PRODUCTION PROCESS

[75] Inventors: Bernard A. Juguin, Rueil Malmaison; Jean-Paul Boitiaux; Germain J. Martino, both of Poissy, all of France

[73] Assignee: Institut Francais du Petrole, Rueil Malmaison, France

[21] Appl. No.: 629,911

[22] Filed: Dec. 19, 1990

[30] Foreign Application Priority Data

Dec. 21, 1989 [FR] France .................. 89 17162

[51] Int. Cl.$^5$ .................. C07C 37/14; C07C 37/16
[52] U.S. Cl. .................. 568/798; 568/741; 568/754; 568/782
[58] Field of Search .............. 568/798, 754, 741, 754, 568/782

[56] References Cited

U.S. PATENT DOCUMENTS

| | | | |
|---|---|---|---|
| 2,668,859 | 2/1954 | Scriabine | 568/798 |
| 2,695,324 | 11/1954 | Langlois | 568/798 |
| 3,029,292 | 4/1962 | Nixon | 568/754 |
| 3,029,293 | 4/1962 | Nixon | 568/754 |
| 4,016,213 | 4/1977 | Yeh et al. | 568/754 |
| 4,083,886 | 7/1978 | Inwood | 585/323 |
| 4,459,426 | 7/1984 | Inwood | 585/323 |
| 4,870,222 | 9/1989 | Bakas | 585/323 |

FOREIGN PATENT DOCUMENTS

| | | | |
|---|---|---|---|
| 0361755 | 4/1990 | European Pat. Off. | 568/798 |
| 0371738 | 6/1990 | European Pat. Off. | 568/798 |

Primary Examiner—Werren B. Lone
Attorney, Agent, or Firm—Millen, White & Zelano

[57] ABSTRACT

Phenol production process wherein:

1) benzene is reacted with propene and isopropylic alcohol by contacting a catalyst based on a dealuminized Y zeolite with a $SiO_2/Al_2O_3$ molar ratio ranging from 8 to 70, then the obtained product is fractionated into a first fraction comprising non converted benzene, a second fraction comprising cumene and a third fraction comprising polyisopropylbenzenes, 2) said third fraction is reacted with benzene by contacting a catalyst based on a dealuminized Y zeolite with a $SiO_2/Al_2O_3$ molar ratio ranging from 8 to 70 or based on a dealuminized mordenite with a total Si/Al atomic ratio ranging from 20 to 60, and cumene is collected, 3) the obtained cumene is converted into a mixture of acetone and phenol, 4) the obtained acetone is at least partly hydrogenized into an isopropylic alcohol which is then recycled at least partly to stage 1.

19 Claims, 1 Drawing Sheet

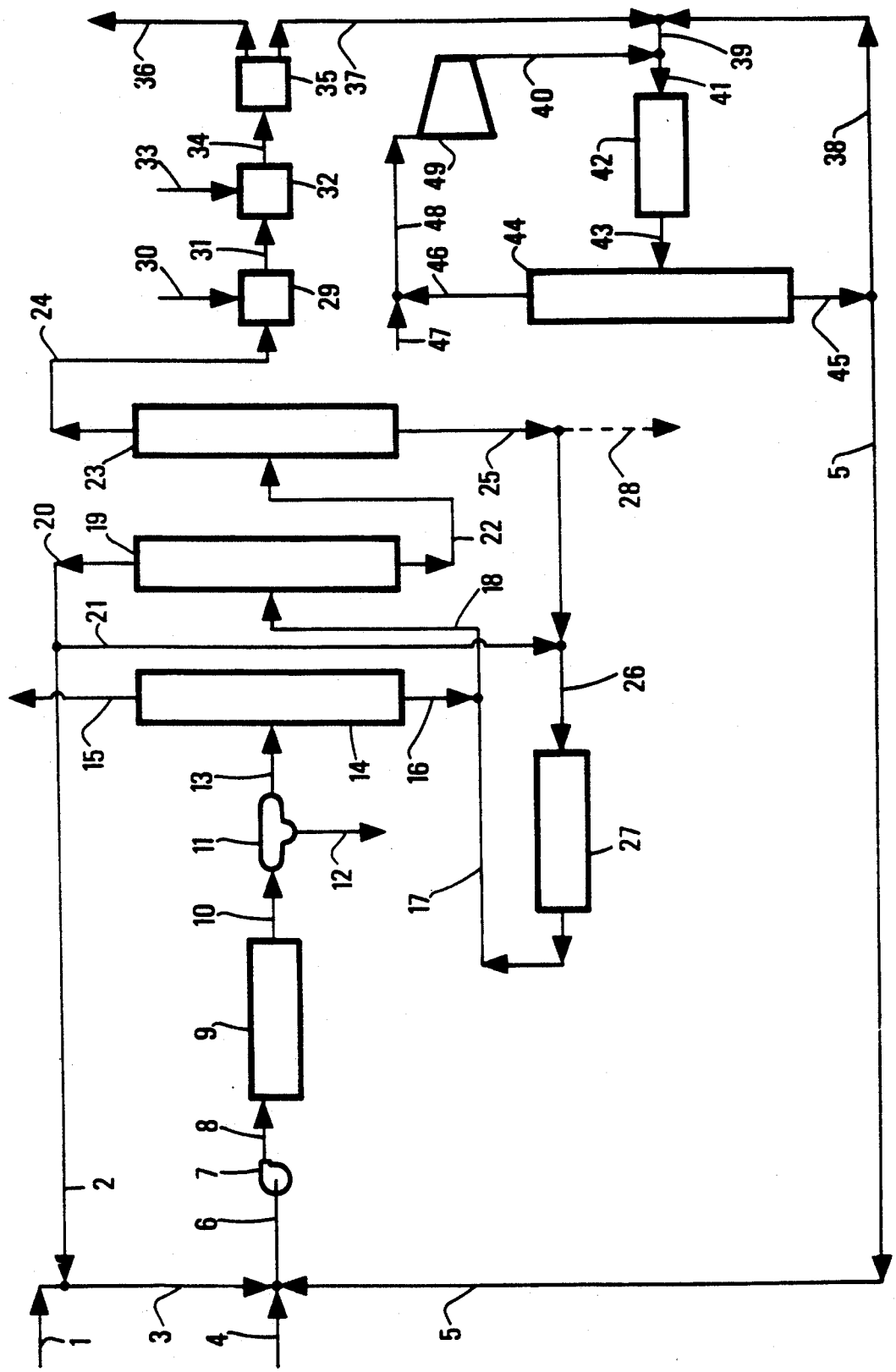

PHENOL PRODUCTION PROCESS

BACKGROUND OF THE INVENTION

The present invention relates to a process for producing phenol through a method utilizing cumene.

There are numerous processes for manufacturing phenol:

1) two of them, the oldest ones, are dying out: the first one comprises the sulfonation of benzene, followed by an alkaline fusion of the obtained sulfonic acid, and the second one, catalytic chlorination, followed by a basic hydrolysis of the obtained chlorobenzene;
2) another process, also rather old, consists in oxidizing the cumene from the reaction of alkylation of benzene by propene;
3) two other processes, more recent, only represent a small part of the world production to date; the first one implements the oxychlorination of benzene, followed by a hydrolysis; the second one converts toluene through a catalytic oxidation with a complex mechanism;
4) lastly, the most recent implements, within a first stage, the oxidation in the liquid phase of cyclohexane, followed, in a second stage, by the catalytic dehydrogenizing of the obtained products.

The most sought-after, in spite of its relative ancientness, remains the process implementing the oxidation of cumene. This process comprises the two following stages:

-the alkylation of benzene by propene into cumene (isopropylbenzene):

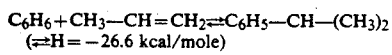

$$C_6H_6 + CH_3-CH=CH_2 \rightleftharpoons C_6H_5-CH-(CH_3)_2$$
$$(\rightleftharpoons H = -26.6 \text{ kcal/mole})$$

-the conversion of cumene into phenol and acetone, which itself comprises two main stages:

.the oxidation of cumene into cumyl hydroperoxide:

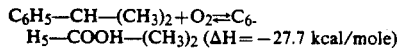

$$C_6H_5-CH-(CH_3)_2 + O_2 \rightleftharpoons C_6H_5-COOH-(CH_3)_2 \quad (\Delta H = -27.7 \text{ kcal/mole})$$

.the cleavage of cumyl hydroperoxide into phenol and acetone:

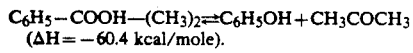

$$C_6H_5-COOH-(CH_3)_2 \rightleftharpoons C_6H_5OH + CH_3COCH_3$$
$$(\Delta H = -60.4 \text{ kcal/mole}).$$

A third stage of advanced purification is also generally carried out because of the increase in the requirements presented by the users who ask for a more and more pure phenol.

Until a recent time, the main advantage of this method utilizing cumene was the technical simplicity of the operation, the high yield in phenol in relation to cumene and the mastery of the process holders in the handling of cumyl hydroperoxide.

Nowadays, the main handicap of this process lies in the obligatory coproduction of 0.61 ton of acetone per ton of phenol, because the demand for phenol increases much more rapidly than that for acetone.

DESCRIPTION OF THE INVENTION

The process according to the invention notably allows to overcome this economic drawback. It consists in partly or totally hydrogenizing the acetone produced into isopropyl alcohol, and in recycling at least partly the latter to the stage of alkylation of benzene where, after dehydration into propene, it will be converted again into cumene. This invention thus allows the production of acetone to be varied from 0 to 0.61 ton per ton of phenol produced.

Until now, the industrial techniques for the alkylation of benzene by propene utilized several types of catalysts, notably aluminum chloride, phosphoric acid deposited on a solid support, silica-aluminas. These various catalysts, which are still used very often, are not adapted to the reaction of alkylation of benzene in the presence of isopropyl alcohol, because they are very sensitive to water; their life in the presence of the water formed by the dehydration of isopropyl alcohol would therefore be very short. Now, only certain zeolites are well adapted to the problem posed, because they are at the same time active and selective, and above all stable in the presence of steam.

According to the process of the invention, benzene is first reacted (first stage or alkylation stage) with a feedstock comprising propene and isopropyl alcohol (this isopropyl alcohol coming at least partly from a further fourth stage) by contacting at least one catalyst based on a dealuminized Y zeolite with a $SiO_2/Al_2O_3$ molar ratio ranging from 8 to 70, then the obtained product is fractionated in order to separately collect a first fraction comprising non converted benzene, a second fraction comprising cumene and a third fraction comprising at least one polyisopropylbenzene (or polyisopropylbenzene fraction).

It may be advantageous to remove at least the most part of the water formed by the dehydration of the isopropyl alcohol into propene during the alkylation stage.

In a second stage (transalkylation stage), at least part of said polyisopropylbenzene fraction is reacted with benzene, for example with benzene at least part of which consists of benzene that has not been converted in the first stage (that is to say non converted benzene from said first fraction obtained in the first stage) or for example with benzene at least part of which does not consist of benzene that has not been converted in the first stage, by contacting at least one catalyst based on a dealuminized Y zeolite with a $SiO_2/Al_2O_3$ molar ratio ranging from 8 to 70, or preferably by contacting at least one catalyst based on a dealuminized mordenite with a total Si/Al atomic ratio ranging from 20 to 60, and cumene is collected.

The excess benzene of the first stage that is not sent to the second stage is advantageously recycled to the first stage, whereas after the second stage, the non converted polyisopropylbenzenes can be at least partly recycled in the same second stage.

Thus, the obtained cumene comes, on one hand, from the second fraction obtained in the first stage and, on the other hand, from the reaction of the third fraction (polyisopropylbenzene fraction) obtained in the first stage with benzene.

In a third stage, the obtained cumene is converted into a mixture of phenol and acetone, then said mixture is fractionated in order to separately collect phenol and acetone.

This third stage comprises the oxidation of cumene into cumyl hydroperoxide (by oxygen for example), then the cleavage of this cumyl hydroperoxide into phenol and acetone (for example under the action of an acid), before the purification and the fractionating of the mixture of phenol and acetone. The phases of oxidation, cleavage and purification are well known by the man skilled in the art.

In a fourth stage, the acetone obtained at the end of the third stage is at least partly (preferably totally) hydrogenized into isopropyl alcohol, preferably in the presence of at least one catalyst based on nickel deposited on a support such as silica or kieselguhr, said isopropyl alcohol being then at least partly recycled towards the first stage of alkylation of benzene.

The dealuminized Y zeolite and the dealuminized mordenite are each used alone or mixed with a binder or a matrix generally selected from the group formed by clays, aluminas, silica, magnesia, zircon, titanium oxide, boron oxide and any combination of at least two of the compounds cited above, such as silica-alumina, silica-magnesia, etc. All the well-known tableting and shaping methods are applicable, such as, for example, extrusion, pelletizing, oil drop, etc.

Thus, in the process according to the invention, at least one catalyst based on a dealuminized Y zeolite with a $SiO_2/Al_2O_3$ molar ratio ranging from 8 to 70, generally containing 1 to 100 %, preferably 20 to 98 % and, for example, 40 to 98 % by weight of said dealuminized Y zeolite and 0 to 99 %, preferably 2 to 80 % and, for example, 2 to 60 % by weight of a matrix is utilized, and possibly at least one catalyst based on a dealuminized mordenite with a total Si/Al atomic ratio ranging from 20 to 60, generally containing 1 to 100%, preferably 20 to 98% and, for example, 40 to 98% by weight of said dealuminized mordenite and 0 to 99%, preferably 2 to 80% and, for example, 2 to 60% by weight of a matrix.

Dealuminized Y zeolites and their preparation are well-known. It can for example be referred to U.S. Pat. No. 4,738,940.

The Y zeolite used in the present invention is an HY acid zeolite characterized by various specifications: a $SiO_2/Al_2O_3$ molar ratio ranging from 8 to 70, and preferably from about 12 to about 40; a sodium content lower than 0.25% by weight determined on the zeolite calcined at 1,100° C.; a crystalline parameter a of the elementary mesh ranging from $24.55 \times 10^{-10}$ to $24.24 \times 10^{-10}$ m and preferably from $24.39 \times 10^{-10}$ to $24.26 \times 10^{-10}$ m; a capacity $C_{Na}$ of recovery of sodium ions, expressed in gram of Na per 100 grams of neutralized, then calcined modified zeolite, higher than about 0.85; a specific surface, determined by the B.E.T. method, higher than about 400 $m^2/g$ and preferably higher than 550 $m^2/g$; a capacity of adsorption of steam at 25° C., for a partial pressure of 2.6 torrs, higher than about 6%; a pore distribution comprising 1 to 20% and preferably 3 to 15% of the pore volume contained in pores with a diameter ranging from $20 \times 10^{-10}$ to $80 \times 10^{-10}$ m, the rest of the pore volume being contained in the pores with a diameter smaller than $20 \times 10^{-10}$ m.

This Y zeolite is for example manufactured, generally from a Y-Na zeolite, through an appropriate combination of two basic treatments: (a) a hydrothermal treatment which combines temperature and partial pressure of the steam, and (b) an acid treatment preferably by a strong and concentrated mineral acid.

The Y-Na zeolite from which the Y zeolite used in the invention is prepared generally shows a $SiO_2/Al_2O_3$ molar ratio ranging from about 4 to 6; it is advisable to previously decrease the content by weight of sodium to less than 3% and preferably to less than 2.5%; the Y-Na zeolite also generally has a specific surface ranging from about 750 to 950 $m^2/g$.

Dealuminized mordenites and their preparation also are well-known. It can for example be referred to European Patents 84,748, 97,552 and 196,965 and to the French patent application of national registration number 87/12,932. The method of dealuminization of the patents or the application cited above consists in subjecting the H form of the mordenite or a precursor of an H form (for example the $NH_4$ form) to a series of thermal treatments in a steam atmosphere and of acid treatments. Nevertheless, unlike the treatments of said documents cited above, the dealuminization rate will be limited to a total Si/Al atomic ratio ranging from 20 to 60. It is preferably operated as follows:

-in a first stage, the non decomposble cations, generally $Na^+$, present in the original mordenite, are removed. To do so, one or several exchanges can be carried out in diluted solutions of acids such as HCl or in $NH_4^+$ solutions, possibly followed by one or several washings (with water for example). The important point is that, at the end of this first stage which may be called decationization, the almost entirety of the alkaline cations is removed (Na content for example ranging from 150 to 2,000 ppm by weight and preferably from 300 to 1,200 ppm by weight) and the obtained solid is an H form or a precursor of an H form (for example $NH_4^+$) substantially not dealuminized (dealuminization rate generally lower than 10% and preferably lower than 5%). As a precursor of the H form, the $NH_4^+$ form will be preferably selected;

-in a second stage, the H form or the precursor of the H form is subjected to a treatment under steam at a temperature higher than 450° C., ranging for example from 450° to 650° C. and preferably from 550° to 600° C. The water content (by volume) in the calcination atmosphere will be advantageously higher than 20% and preferably higher than 40%;

-the acid attack is the third stage of the preparation of catalysts. For structure Si/Al atomic ratios (of the solid after calcination) up to about 50, concentrations of acid solutions (HCl, $H_2SO_4$, $HNO_3$, etc.) ranging from 0.5 to 5 N and preferably from 1 to 4 N, will be preferably used. For higher structure Si/Al atomic ratios, concentrations of acid solutions ranging from 5 to 20 N and preferably from 7 to 12 N (the structure Si/Al atomic ratios can be determined by infrared spectroscopy for ratios ranging from 10 to 50 and by NMR of the $^{29}Si$ for higher ratios) will be used. Besides, in order to reach high Si/Al atomic ratios, that is to say higher than about 50, several calcination under steam-acid attack cycles can be advantageously carried out.

The solids prepared thereby advantageously show total Si/Al atomic ratios ranging from 20 to 60; their elementary mesh volume ranges from 2.755 to 2.730 $nm^3$ (1 nm = $10^{-9}$ m) and preferably from 2.745 to 2.735 $nm^3$; their acid strength is preferably sufficient for the structural Al-OH to interact with a weak base such as ethylene (infrared measuring at 77 K) or a little acid compound such as $H_2S$ (infrared measuring at 25° C.). These solids must also be preferably free from extra-lattice cationic species which can be detected by a fine signal (width at half-height smaller than 5 ppm and preferably smaller than 2 ppm) located at 0 ppm (reference $Al(H_2O)_6^{3+}$) on a NMR spectrum of $^{27}Al$, measured with the technique of rotation of the magic angle.

The reaction known as alkylation (first stage of the process according to the invention) is usually performed in the liquid phase, in the supercritical phase or in the gaseous phase, in the presence of at least one catalyst based on the dealuminized Y zeolite defined above, arranged in a fixed bed, at a temperature ranging from about 100° to 350° C. (preferably from about 180° to 300° C.), under a pressure ranging from 1 to 10 MPa (preferably from 2 to 7 MPa), with a liquid hydrocarbon flow rate (space velocity) ranging from about 0.5 to 20 volumes per volume of catalyst and per hour, and with a benzene/(propene+isopropyl alcohol) molar ratio ranging from 1 to 20 (preferably from 5 to 12).

The reaction known as transalkylation of the polyisopropylbenzenes (second stage of the process according to the invention) formed during the alkylation stage is usually carried out in the presence of at least one catalyst based o the dealuminized Y zeolite defined above or preferably based on the dealuminized mordenite answering the general features described above, arranged in a fixed bed, at a temperature ranging from about 250° to 500° C. (preferably from about 300° to 420° C.), under a pressure ranging from 2 to 10 MPa (preferably from 2.5 to 7 MPa), with a liquid hydrocarbon flow rate (space velocity) ranging from about 0.3 to 5 volumes per volume of catalyst and per hour, and with a benzene/polyisopropylbenzenes molar ratio ranging from 2 to 50 (preferably from 5 to 20).

The reaction of hydrogenation of acetone into isopropyl alcohol (fourth stage of the process according to the invention) is usually performed in the presence of at least one catalyst based on nickel deposited on a support such as silica or kieselguhr, generally containing 3 to 70%, preferably 8 to 60%, and for example 12 to 25% by weight of nickel (this catalyst can be used in the form of balls, pellets or extrudates), arranged in a fixed bed, at a temperature ranging from about 40° to 200° C. (preferably from about 60° to 160° C.), under a pressure ranging from 1.5 to 10 MPa (preferably from 2 to 6 MPa), with an hourly flow rate of liquid hydrocarbons (recycled acetone+possibly isopropyl alcohol) of about 1 to 5 times the weight of the catalyst, with a hydrogen/acetone molar ratio ranging from 1 to 20 (preferably from 3 to 8). The reaction of hydrogenation of acetone being exothermal, the temperature rise between the inlet and the outlet of the hydrogenation reactor is generally limited to a value ranging from about 30° to 70° C. in order not to risk a racing of the reaction; to do so, at least part of the isopropyl alcohol formed at the inlet of the hydrogenation reactor is generally recycled, with an isopropyl alcohol/acetone molar ratio at the inlet of said reactor ranging from 2 to 20 (preferably from 4 to 15).

DESCRIPTION OF DRAWING

The sole FIGURE illustrates a particular embodiment of the invention: fresh benzene (1) is mixed with recycled benzene (2) coming from the head of a distillation column (19); the resulting mixture (3) is then mixed with fresh propene (4) and with isopropyl alcohol (5) coming from the bottom of a distillation column (44). The obtained mixture (6) is then sent, by means of a pump (7), to the alkylation reactor (9) through pipe (8), after passing in a heating oven not shown on the FIGURE. At the outlet of the alkylation reactor (9), the effluent is introduced through pipe (10) into a decanting flask (11). At the bottom of the decanting flask (11), most part of the water formed after the dehydration of the isopropyl alcohol into propene is withdrawn through pipe (12). The supernatant hydrocarbon fraction is then sent, through pipe (13), towards a first distillation column (14) acting as a depropanizer; at the top of this first distillation column (14), a mixture formed by steam, propane and propene non converted during the alkylation reaction is recovered through pipe (15). At the bottom of this distillation column (14), a mixture of non converted benzene and of alkylbenzenes (cumene, polyisopropyl-benzenes) is withdrawn through pipe (16) and then mixed with hydrocarbons coming from the transalkylation reactor (27) through pipe (17). The resulting mixture is then sent, through pipe (18), towards a second distillation column (19). At the top of this second distillation column (19), the excess benzene non converted in the alkylation reactor is collected through pipe (20); this benzene is partly recycled, through pipe (2), towards the alkylation reactor (9), the other part being sent, through pipe (21), towards the reactor of transalkylation of the polyisopropylbenzenes (27). At the bottom of this second distillation column (19), a mixture of cumene and polyisopropylbenzenes is withdrawn through pipe (22) and sent towards a third distillation column (23). At the top of this third distillation column (23), pure cumene is collected and sent, through pipe (24), towards the reactor for the oxidation of the cumene (29). At the bottom of this third distillation column (23), a product consisting of diiso-propylbenzenes and triisopropylbenzenes is withdrawn through pipe (25) and sent, after mixing with the recycled benzene through pipe (21), towards the reactor of transalkylation of the polyisopropylbenzenes (27) through pipe (26). If necessary, a part of the polyisopropylbenzenes can be optionally purged out of the circuit through pipe (28). The cumene coming from the top of the third distillation column (22) through pipe (24) enters then the oxidation reactor (29), where it is converted into cumyl hydroperoxide (oxygen supply through pipe (30)), which is then sent, through pipe (31), into the cleavage section (32) in order to be converted there into a mixture of phenol and acetone (acid supply through pipe (33)). This mixture is then sent, through pipe (34), into a section (35) in order to be purified and separated by fractionating. At the outlet of purification and fractionating section (35), pure phenol that is sent through pipe (36) to the storage facility is collected on one hand, and pure acetone is collected on the other hand (pipe (37)). This pure acetone is then mixed with isopropyl alcohol (used as a diluent) coming from the bottom of a fourth distillation column (44) through pipes (45), then (38). The resulting mixture (39) is then mixed with hydrogen under pressure coming from a compressor (49) through pipe (40). The hydrogen entering the compressor (49) through pipe (48) is made, on one hand, by recycling hydrogen coming from the top of the fourth distillation column (44) through pipe (46) and, on the other hand, by fresh hydrogen coming through pipe (47). The mixture acetone-isopropyl alcohol-hydrogen is introduced, through pipe (41), into the hydrogenation reactor (42). The effluent of the hydrogenation reactor (42) is then sent through pipe (43) into the fourth distillation column (44). At the top of this fourth column (44), the non converted hydrogen is collected through pipe (46). At the bottom of this fourth distillation column (44), isopropyl alcohol is withdrawn through pipe (45); part of this alcohol is recycled, through pipe (38), towards the hydrogenation reactor (42) to serve as a diluent, the other part being sent, through pipe (5), towards the reactor of alkylation of the benzene (9).

The following non limitative examples illustrate the invention without limiting the scope thereof.

EXAMPLE 1: Preparation of a catalyst A

The raw material which is used is a NaY zeolite of formula Na, $AlO_2$ $(SiO_2)_{2.5}$.

This zeolite shows the following characteristics:
-$SiO_2/Al_2O_3$ molar ratio: 5
-crystalline parameter a: $24.69 \times 10^{-10}$ m
-capacity for adsorbing steam at 25° C. (at P/Po=0.1): 26%
-specific surface: 880 m²/g.

It is subjected to five consecutive exchanges in solutions of ammonium nitrate with a concentration of 2M, at a temperature of 95° C., for a duration of 1.5 hour, and with a volume of solution to weight of zeolite ratio of 8 cm³/g. The sodium rate of the obtained $NaNH_4Y$ zeolite is 0.95%. This product is then rapidly introduced into an oven preheated at 770° C. and left for 4 hours in a static atmosphere (stabilizing treatment). The zeolite is then subjected to an acid treatment in the following conditions: the ratio between the volume of solution of nitric acid 2N and the weight of the solid is 6 cm³/g, the temperature is 95° C. and the treatment lasts 3 hours. Another treatment is then carried out under the same conditions, but with a solution of nitric acid 0.3N.

The obtained zeolite has a content by weight of sodium of 0.2%, a $SiO_2/Al_2O_3$ molar ratio of 18, a crystalline parameter a of the elementary mesh of $24.32 \times 10^{-10}$ m, a specific surface of 805 m²/g, a capacity of recovery of water of 13.7% (at P/Po=0.1), a capacity of recovery of sodium ions of 2 and 9% of its pore volume is contained in pores with a diameter ranging from $20 \times 10^{-10}$ to $80 \times 10^{-10}$ m, the rest of its pore volume being contained in pores with a diameter smaller than $20 \times 10^{-10}$ m.

This zeolite is then shaped by extrusion with alumina. The obtained extrudates are then dried and calcined at about 500° C. A catalyst A based on said zeolite, containing 80% by weight of said zeolite and 20% by weight of alumina, is then obtained.

EXAMPLE 2: Preparation of a catalyst B

The raw material utilized to prepare this catalyst is a small-pore mordenite manufactured by the Société Chimique de la Grande Paroisse, reference Alite 150; its chemical formula in the anhydrous state is Na, $AlO_2$ $(SiO_2)_{2.5}$ and its content by weight of sodium is 5.3%. 500 grams of this powder are plunged into a 2M solution of ammonium nitrate, and the suspension is brought up to 95° C. for 2 hours. The volume of the solution of ammonium nitrate used is four times the weight of the dry mordenite (V/W=4 g/cm³). This operation of cationic exchange is performed 3 times. After the 3rd exchange, the product is washed with water at 20° C. for 20 minutes, with a V/W ratio of 4 g/cm³. The sodium content expressed in percentage by weight in relation to the dry mordenite no longer exceeds 0.1%. The product is then filtered and subjected to a self-steaming calcination at 560° C. for 2 hours. The water content (by volume) of the calcination atmosphere is about 90%. The crystallinity of this solid, after this calcination stage, is greater than or equal to 90%, its structure Si/Al atomic ratio is 49.

This solid is then subjected to an acid attack by means of a 3.5N solution of nitric acid. During the acid attack, the solid is thus injected as a reflux into the solution of nitric acid for 2 hours, with a V/W ratio of 8 g/cm³. The product is then filtered and abundantly washed with distilled water.

The obtained mordenite has a total Si/Al atomic ratio of 49; its volume of elementary mesh equals 2.74 nm³.

It is then shaped by malaxing with alumina, then by passing through a die. The obtained extrudates, with a diameter of 1.2 mm, are then dried and calcined between 150° and 500° C. by steps of about one hour. A catalyst B based on said mordenite, containing 80% by weight of said mordenite and 20% by weight of alumina, is thus obtained.

EXAMPLE 3

A feedstock is fed into an alkylation reactor containing catalyst A.

The operating conditions is the alkylation reactor are the following:

| | |
|---|---|
| temperature | 240° C. |
| pressure | 4 MPa |
| hourly flow rate of benzene equals 2 times the volume of catalyst | |
| benzene/propene molar ratio | 8.4. |

The feedstock has the following composition by weight:

| | |
|---|---|
| propane | 0.31% |
| propene | 6.00% |
| benzene | 93.69%. |

At the outlet of the alkylation reactor, the obtained product has the following composition by weight:

| | |
|---|---|
| propane | 0.31% |
| propene | — |
| benzene | 82.99% |
| cumene | 15.83% |
| diisopropylbenzenes | 0.77% |
| triisopropylbenzenes | 0.10%. |

The obtained product is then fractionated by distillation and two fractions are gathered:
-an initial point −160° C. fraction containing the non converted benzene and the cumene, the cumene being then separated from said fraction,
-a fraction with a boiling point higher than 160° C. containing the polyisopropylbenzenes.

This fraction with a boiling point higher than 160° C. is then subjected to a transalkylation treatment in the presence of catalyst B prepared in example 2.

The operating condition in the transalkylation reactor are the following:

| | |
|---|---|
| temperature | 350° C. |
| pressure | 4 MPa |
| hourly flow rate of (benzene + polyisopropyl-) benzenes) equals 1 times the volume of the catalyst | |
| benzene/polyisopropylbenzenes molar ratio | 15. |

The feedstock thus has the following composition by weight:

| | |
|---|---|
| benzene | 6.13 |
| diisopropylbenzenes | 0.77 |
| triisopropylbenzenes | 0.10 |
| | 7 |

At the outlet of the transalkylation reactor, the obtained product has the following composition by weight:

| | |
|---|---|
| benzene | 5.79 |
| cumene | 1.10 |
| diisopropylbenzenes | 0.08 |
| triisopropylbenzenes | 0.03 |
| | 7 |

The overall results combining the two stages of alkylation on one hand and of transalkylation on the other hand are the following:

| | |
|---|---|
| propane | 0.31% |
| propene | — |
| benzene | 82.65% |
| cumene | 16.93% |
| diisopropylbenzenes | 0.08% |
| triisopropylbenzenes | 0.03% |
| conversion rate of benzene | 11.8% |
| conversion rate of propene | 100% |
| cumene selectivity in relation to the converted propene | 98.8% |
| cumene selectivity in relation to the converted benzene | 99.7% |

According to the data published in the scientific and commercial literature (Procédés de Pétrochimie, Société des éditions TECHNIP, 1971, p.356), 16.93 kg of cumene would lead, after oxidation, acid cleavage, purifications and fractionatings, to the joint production of 12.05 kg of pure phenol and 7.38 kg of acetone, which corresponds to specific consumptions, per ton of pure phenol produced, of 0.497 ton of propene and 0.916 ton of benzene.

EXAMPLE 4

A catalyst consisting of extrudates containing 20% by weight of nickel and 80% by weight of silica is utilized for the reaction of hydrogenation of the acetone into isopropyl alcohol.

The operating conditions in the hydrogenation reactor are the following:

| | |
|---|---|
| inlet temperature in the reactor | 80° |
| outlet temperature of the reactor | 130° |
| operating pressure | 4 MPa |
| isopropyl alcohol/acetone molar ratio | 6.6 |
| hourly flow rate of (acetone + isopropyl alcohol) feedstock equals 2 times the weight of the catalyst | |
| hydrogen/acetone molar ratio | 5. |

The feedstock thus has the following composition by weight:

| | |
|---|---|
| hydrogen | 2.19% |
| isopropyl alcohol | 85.09% |
| acetone | 12.72% |

At the outlet of the hydrogenation reactor, the obtained product has the following composition by weight:

| | |
|---|---|
| hydrogen | 1.75% |
| isopropyl alcohol | 98.25%. |

The reaction is thus quantitative.

In the case of example 3, 7.38 kg of acetone thus lead to the production of 7.63 kg of isopropyl alcohol.

EXAMPLE 5

Catalyst A prepared in example 1 is utilized for the reaction of alkylation of benzene by isopropyl alcohol.

The operating conditions in the alkylation reactor are the following:

| | |
|---|---|
| temperature | 240° C. |
| pressure | 4 MPa |
| hourly flow rate of the (benzene + isopropylic alcohol) feedstock equals 2 times the volume of the catalyst | |
| benzene/isopropyl alcohol molar ratio | 8.8. |

The feedstock at the inlet of the alkylation reactor thus has the following composition by weight:

| | |
|---|---|
| benzene | 92% |
| isopropyl alcohol | 8%. |

At the outlet of the alkylation reactor, the obtained product has the following composition by weight:

| | |
|---|---|
| water | 2.40% |
| propene | 0.05% |
| benzene | 82.64% |
| cumene | 13.14% |
| diisopropylbenzenes | 1.45% |
| triisopropylbenzenes | 0.32% |

After the reaction, the formed water is separated by decantation, then the hydrocarbon phase is fractionated by distillation, and two fractions are collected:
- an initial point $-160°$ C. fraction containing the non converted benzene and the cumene, the cumene being then separated from said fraction,
- a fraction with a boiling point higher than 160° C. containing the polyisopropylbenzenes.

This fraction with a boiling point higher than 160° C. is then subjected to a transalkylation treatment in the presence of catalyst B prepared in example 2.

The operating conditions in the transalkylation reactor are the following:

| | |
|---|---|
| temperature | 350° C. |
| pressure | 4 MPa |
| hourly flow rate of (benzene + polyisopropylbenzenes) equals 1 times the volume of the catalyst, | |
| benzene/polyisopropylbenzenes molar ratio | 15. |

The feedstock thus has the following composition by weight:

| | |
|---|---|
| benzene | 12.31 |

-continued

| | |
|---|---|
| diisopropylbenzenes | 1.45 |
| triisopropylbenzenes | 0.32 |
| | 14.08 |

At the outlet of the transalkylation reactor, the obtained product has the following composition by weight:

| | |
|---|---|
| benzene | 11.65 |
| cumene | 2.18 |
| diisopropylbenzenes | 0.15 |
| triisopropylbenzenes | 0.10 |
| | 14.08 |

The overall results combining the two stages of alkylation on one hand and of transalkylation on the other hand are the following:

| composition by weight of the product: | |
|---|---|
| water | 2.40% |
| propene | 0.05% |
| benzene | 81.98% |
| cumene | 15.32% |
| diisopropylbenzenes | 0.15% |
| triisopropylbenzenes | 0.10% |
| conversion rate of the benzene | 10.9% |
| conversion rate of isopropyl alcohol | 100% |
| cumene selectivity in relation to the converted isopropyl alcohol | 95.8% |
| cumene selectivity in relation to the converted benzene | 99.4% |

After oxidation, acid cleavage, purifications and fractionatings, 15.32 kg of cumene would lead to the joint production of 10.91 kg of pure phenol and 6.68 kg of acetone, which corresponds to specific consumptions, per ton of pure phenol produced, of 0.733 ton of isopropyl alcohol and 0.918 ton of benzene.

EXAMPLE 6

According to the invention, catalyst A prepared in example 1 is utilized for the reaction of alkylation of the benzene by a mixture of propene and isopropyl alcohol. The isopropyl alcohol/propene ratio by weight corresponds to the results obtained in examples 3 and 4.

The operating conditions in the alkylation reactor are the following:

| | |
|---|---|
| temperature | 240° C. |
| pressure | 4 MPa |
| hourly flow rate of the (benzene + propene + isopropylic alcohol) feedstock equals 2 times the volume of the catalyst | |
| benzene/(propene + isopropyl alcohol) molar ratio | 8.4. |

The feedstock at the inlet of the alkylation reactor thus has the following composition by weight:

| | |
|---|---|
| propane | 0.15% |
| propene | 3.13% |
| isopropyl alcohol | 3.99% |
| benzene | 92.73%. |

At the outlet of the alkylation reactor, the obtained product has the following composition by weight:

| | |
|---|---|
| water | 1.20% |
| propane | 0.15% |
| propene | 0.03% |
| benzene | 82.49% |
| cumene | 14.80% |
| diisopropylbenzenes | 1.12% |
| triisopropylbenzenes | 0.21% |

After the reaction, the formed water is separated by decantation, then the hydrocarbon phase is fractionated by distillation, and two fractions are collected:
-an initial point −160° C. fraction containing the non converted benzene and the cumene, the cumene being then separated from said fraction,
-a fraction with a boiling point higher than 160° C. containing the polyisopropylbenzenes.

This fraction with a boiling point higher than 160° C. is then subjected to a transalkylation treatment in the presence of catalyst B prepared in example 2.

The operating conditions in the transalkylation reactor are the following:

| | |
|---|---|
| temperature | 350° C. |
| pressure | 4 MPa |
| hourly flow rate of benzene + polyisopropylbenzenes equals 1 times the volume of the catalyst | |
| benzene/polyisopropylbenzenes molar ratio | 15. |

The feedstock thus has the following composition by weight:

| | |
|---|---|
| benzene | 9.29 |
| diisopropylbenzenes | 1.12 |
| triisopropylbenzenes | 0.21 |
| | 10.62 |

At the outlet of the transalkylation reactor, the obtained product has the following composition by weight:

| | |
|---|---|
| benzene | 8.78 |
| cumene | 1.67 |
| diisopropylbenzenes | 0.11 |
| triisopropylbenzenes | 0.06 |
| | 10.62 |

The overall results combining the two stages of alkylation and transalkylation are the following:

| composition by weight of the product: | |
|---|---|
| water | 1.20% |
| propane | 0.15% |
| propene | 0.03% |
| benzene | 81.98% |
| cumene | 16.47% |
| diisopropylbenzenes | 0.11% |
| triisopropylbenzenes | 0.06% |
| conversion rate of the benzene | 11.6% |
| conversion rate of the propene | 99% |
| conversion rate of the isopropyl alcohol | 100% |
| cumene selectivity in relation to the sum converted propene + isopropyl alcohol | 97.8% |
| cumene selectivity in relation to the converted benzene | 99.6% |

After oxidation of the cumene, acid cleavage of the cymel hydroperoxide, purifications and fractionatings, 16.37 kg of cumene lead to the production of 11.73 kg of pure phenol, which corresponds to specific consumptions, per ton of pure phenol produced, of 0.267 ton of propene and 0.916 ton of benzene.

By comparing the results obtained in exemples 3 and 6, it can be seen that it is very advantageous to work according to the invention, because:

1) it is possible to obtain pure phenol without jointly producing acetone,
2) for the same specific consumption of benzene, the specific consumption of propene is reduced by 46%.

According to the market fluctuations, it is also possible to balance the joint production of acetone on request, by acting on the recycling rate of this co-product towards the hydrogenation unit. The invention thus notably gives a great operating flexibility in this type of process.

What is claimed is:

1. A process for producing phenol, comprising the following successive steps:
   (1) benzene is reacted in an alkylation step with a feedstock comprising propene and isopropyl alcohol by contacting at least one catalyst based on a dealuminzed Y zeolite with an $SiO_2/Al_2O_3$ molar ratio ranging from 8 to 70 at a temperature of from about 100°-350° C. under a pressure of from 1-10 mPa, then the obtained product is fractionated in order to separately collect a first fraction comprising non-converted benzene, a second fraction comprising cumene and a third fraction comprising at least one polyisopropylbenzene,
   (2) at least part of said third fraction in a transalkylation step separate from said alkylation step is reacted with benzene by contacting at least one catalyst based on a dealuminized Y zeolite with an $SiO_2/Al_2O_3$ molar ratio ranging from 8 to 70 at a temperature of from about 250°-500° C. under a pressure of from 2-10 mPa, and cumene is collected,
   (3) the cumene coming from steps (1) and (2) is oxidized with air to obtain cumyl hydroperoxide, said hydroperoxide is cleaved with an acid to obtain a mixture of phenol and acetone, then said mixture is fractionated in order to separately collect phenol and acetone,
   (4) the acetone obtained at the end of step (3) is at least partly hydrogenized at a temperature of from about 40°-200° C. under a pressure of from 1.5-10 mPa into isopropyl alcohol that is then at least partly recycled directly to step (1).

2. A process for producing phenol, comprising the following successive steps:
   (1) benzene is reacted in an alkylation step with a feedstock comprising propene and isopropyl alcohol by contacting at least one catalyst based on a dealuminized Y zeolite with an $SiO_2/Al_2O_3$ molar ratio ranging from 8 to 70 at a temperature of from about 100°-350° C. under a pressure of from 1-10 mPa, then the obtained product is fractionated in order to separately collect a first fraction comprising non-converted benzene, a second fraction comprising cumene and a third fraction comprising at least one polyisopropylbenzene,
   (2) at least part of said third fraction in a transalkylation step separate from said alkylation step is reacted with benzene by contacting at least one catalyst based on a dealuminized mordenite with a total Si/Al atomic ratio ranging from 20 to 60 at a temperature of from about 250°-500° C. under a pressure of from 2-10 mPa, and cumene is collected,
   (3) the cumene coming from steps (1) and (2) is oxidized with air to obtain cumyl hydroperoxide, said hydroperoxide is cleaved with an acid to obtain a mixture of phenol and acetone, then said mixture is fractionated in order to separately collect phenol and acetone,
   (4) the acetone obtained at the end of step (3) is at least partly hydrogenized at a temperature of from about 40°-200° C. under a pressure of from 1.5-10 mPa into alcohol that is then at least partly recycled directly to step (1).

3. A process according to claim 1, wherein at least part of the benzene utilized in step (2) consists of non converted benzene from said first fraction obtained at the end of stage (1).

4. A process according to claim 1, wherein the polyisopropylbenzenes not converted during, step (2) are at least partly recycled in said step (2).

5. A process according to claim 1, wherein the conversion of the cumene into a mixture of phenol and acetone during stage (3) comprises the oxidation of the cumene into cumyl hydroperoxide, then the cleavage of said cumyl hydroperoxide into a mixture of phenol and acetone.

6. A process according to claim 1, wherein hydrogenation step (4) is carried cut in the presence of at least one catalyst based on nickel deposited on a support.

7. A process according to claim 1, wherein at least the most part of the water formed by the dehydration of isopropyl alcohol into propene during step (1) is removed at the end of step (1).

8. A process according to claim 1, wherein each catalyst is arranged in a fixed bed.

9. A process for producing pure phenol according to claim 1, without jointly producing acetone.

10. A process according to claim 1, wherein the transalkylation step is conducted at a higher temperature than the alkylation step.

11. A process according to claim 1, wherein the alkylation step is conducted with a catalyst having an $SiO_2/Al_2O_3$ molar ratio of above 10.

12. A process according to claim 2, wherein at least part of the benzene utilized in step (2) consists of non-converted benzene from said first fraction obtained at the end of step (1).

13. A process according to claim 2, wherein the polyisopropylbenzenes not converted during step (2) are at least partly recycled in said step (2).

14. A process according to claim 2, wherein hydrogenation step (4) is carried out in the presence of at least one catalyst based on nickel deposited on a support.

15. A process according to claim 2, wherein at least the most part of the water formed by the dehydration of isopropyl alcohol into propene during step (1) is removed at the end of step (1).

16. A process according to claim 2, wherein each catalyst is arranged in a fixed bed.

17. A process for producing pure phenol according to claim 2, without jointly producing acetone.

18. A process according to claim 2, wherein the transalkylation step is conducted at a higher temperature than the alkylation step.

19. A process according to claim 2, wherein the alkylation step is conducted with a catalyst having an $SiO_2/Al_2O_3$ molar ratio of above 10.

* * * * *